United States Patent [19]
Tucci et al.

[11] Patent Number: 6,015,570
[45] Date of Patent: Jan. 18, 2000

[54] SLOW-RELEASE INSECT-REPELLENT COMPOSITIONS AND USES

[75] Inventors: Raymond J. Tucci, Yardley, Pa.; Nathan M. Dry, Greensboro, N.C.

[73] Assignee: Tucci Associates, Inc., Yardley, Pa.

[21] Appl. No.: 09/137,426

[22] Filed: Aug. 20, 1998

Related U.S. Application Data

[63] Continuation-in-part of application No. 08/663,267, Dec. 12, 1994, abandoned, which is a continuation-in-part of application No. 08/173,416, Dec. 23, 1993, abandoned.

[51] Int. Cl.$^7$ ................................................. A01N 25/34
[52] U.S. Cl. .................... 424/403; 424/411; 424/418; 424/DIG. 10; 514/617; 514/919; 442/60; 442/123; 442/124; 442/125
[58] Field of Search ................... 442/60–63, 123–125; 524/506, 536, 52; 528/38, 361; 514/919, 617; 424/409–418, DIG. 10; 2/4, 900

[56] References Cited

U.S. PATENT DOCUMENTS

| | | | |
|---|---|---|---|
| 2,214,962 | 9/1940 | Jones | 442/125 |
| 2,707,689 | 5/1955 | Wilde | 442/125 |
| 3,130,121 | 4/1964 | Rapport | 424/418 |
| 3,769,060 | 10/1973 | Ida et al. | |
| 3,859,121 | 1/1975 | Yeadon et al. | |
| 3,995,034 | 11/1976 | Strobel | |
| 4,056,610 | 11/1977 | Barber, Jr. et al. | |
| 4,382,813 | 5/1983 | Shasha | 71/88 |
| 4,594,286 | 6/1986 | McKinney et al. | |
| 4,765,982 | 8/1988 | Ronning et al. | |
| 4,774,090 | 9/1988 | Fekete et al. | 424/408 |
| 4,833,006 | 5/1989 | McKinney et al. | |
| 5,003,635 | 4/1991 | Peterson | |
| 5,089,298 | 2/1992 | McNally et al. | |
| 5,145,675 | 9/1992 | Won | |
| 5,156,843 | 10/1992 | Leong et al. | 424/411 |
| 5,182,304 | 1/1993 | Steltenkamp | |
| 5,194,265 | 3/1993 | Boettcher et al. | |
| 5,198,287 | 3/1993 | Samson et al. | |
| 5,218,002 | 6/1993 | Stroech et al. | |
| 5,221,535 | 6/1993 | Domb | |
| 5,227,163 | 7/1993 | Eini et al. | |
| 5,227,406 | 7/1993 | Beldock et al. | |
| 5,238,682 | 8/1993 | Akasaka et al. | 424/409 |
| 5,518,736 | 5/1996 | Magdassi et al. | 424/451 |

OTHER PUBLICATIONS

Mitoubishi JP 04263617, Sep. 1992.
Tucci, et al WO 95/17091 Slow–Release Insect–Repellent Fabric Composition and Related Methods Publication Jun. 29, 1995.

*Primary Examiner*—Neil S. Levy
*Attorney, Agent, or Firm*—Reed Smith Shaw & McClay LLP

[57] ABSTRACT

A slow-release insect repellent composition comprising an insect repellent, an oleophilic chemical soluble in the insect repellent, and a carbohydrate matrix wherein the combination of the insect repellent and oleophilic chemical is entrapped in the matrix such that the repellent is released from the matrix, a fabric substrate containing the composition and method for preparing the composition.

17 Claims, No Drawings

SLOW-RELEASE INSECT-REPELLENT COMPOSITIONS AND USES

CROSS-REFERENCE TO RELATED APPLICATION

This is a continuation-in-part of U.S. application Ser. No. 08/663,267, filed Dec. 22, 1994, now abandoned which in turn is a continuation-in-part of U.S. application Ser. No. 08/173,416 filed Dec. 23, 1993 now abandoned entitled "SLOW-RELEASE INSECT-REPELLENT COMPOSITIONS AND USES."

FIELD OF THE INVENTION

The present invention relates to fabric substrates such as woven, non-woven, and knit substrates that are treated with an insect-repellent composition comprising amine insect repellents such as N,N'-diethyl-m-toluamide, at least two reactive silicones, and starch.

BACKGROUND OF THE INVENTION

There is a universal need for outdoor fabrics suitable for apparel use and providing for long term insect repellency. Although many insect repellents are effective when applied to the skin as a spray or lotion, their effectiveness is known to decline with time. Furthermore, in order for an insect repellent to be effective, the insect repellant must be applied in a concentrated amount to a small area of the face, neck, or hands or on selected areas of a wearer's garment.

The effectiveness of insect repellents has been known to improve when such repellents are directly applied to fabrics which are suitable for outdoor use, and various techniques have been suggested for providing sustained release of an insect control agent.

For example, in U.S. Pat. No. 4,056,610 to Barber, et al., the invention provides for a microcapsular insecticidal composition comprising a pyrethroid and a biological synergist capable of controlling insects for up to four (4) days.

In U.S. Pat. No. 5,198,287 to Samson, the invention provides for a tent fabric coated on the inside with a composition which renders it water repellent, flame retardant and insecticide using permethrin as the insecticide. Permethrin is protected against oxygen with a plasticizer. The outside of the tent is coated with a composition which renders it water repellent and flame retardant exclusive of the insecticide. The insecticide composition has an effective life of more than six (6) months.

In U.S. Pat. No. 4,765,982 to Ronning, the invention relates to compositions, devices and methods for controlling insect activity wherein an insect control agent is self-adhered to a rough-surfaced fiber and provides extended control of insect activity. The microencapsulated insect control agents disclosed in Barber are named as the preferred insect control for use in Ronning's invention. Ronning teaches that smooth-surfaced fibers do not act as good sites for adhesion of microencapsulated insect control agents.

In U.S. Pat. No. 5,003,635 to Peterson, the invention relates to elongated flexible insect-repellent strips secured to or retained in cavities in various articles of apparel to repel insects from the person wearing such apparel.

In U.S. Pat. No. 4,833,006 to McKinney, the invention relates to a coated fabric that is flame resistant and water repellent and includes a polyfunctional isocyanate as an adhesion promoter and binder to adhere the coating to the substrate in a flake proof manner.

In U.S. Pat. No. 5,089,298 to McNally, the invention relates to the impregnation of Battle Dress Uniforms used by the U.S. Military with amylopectin fabric wrinkle inhibitor and permethrin insect/arthropod repellent in combination.

In U.S. Pat. No. 3,859,121 to Yeadon et al., the invention relates to textiles impregnated with insect-repellent compositions including piperonyl butoxide and pyrethrin, wetting agent, thickener and an agent for preventing migration of the piperonyl butoxide and pyrethrin repellent into foods stored in contact with the textiles and for otherwise retaining the repellent in the textiles.

An amine insect repellent such as, for example, N,N'-diethyl-m-toluamide (DEET) is an effective insect repellent. In addition, it is believed that DEET is generally environmentally safe and leaves no or minimal harmful residues. DEET has been found to be stable at both reduced and elevated temperatures and under storage conditions. DEET is effective on biting flies, chiggers, deerflies, fleas, leeches, mosquitoes, and ticks. Several factors influence the efficacy of DEET as an insect repellent, such as, for example, extreme environmental conditions, the extent of absorption and elimination, the type of repellent composition, and the avidity of the test species. Typically, the efficacy of DEET tends to be reduced by increased perspiration and external water sources such as rain.

SUMMARY OF THE INVENTION

One object of the present invention is to provide an insect-repellent composition and process of making same such that the insect repellent is slowly released. It is a further object of this invention to provide for slow-release insect-repellent compositions and a process of manufacturing same that may be applied to a fabric substrate such as woven, non-woven and knit substrates and result in slow-release of the insect repellent from the fabric.

The present invention relates to a fabric composition comprising a fabric substrate and an insect-repellent composition, wherein the insect-repellent composition comprises an amine insect repellent, at least one reactive silicone, and starch.

The present invention relates to a fabric composition comprising: (a) a fabric substrate; and (b) an application of an aqueous composition formed by an insect-repellent composition consisting essentially of an amine insect-repellent, at least one reactive silicone, and starch. The reactive silicones, of the insect-repellent composition may comprise a substituted organosilane and silanol functional polymer. The starch of the insect-repellent composition may be modified corn starch. The amine insect-repellent of the insect-repellent composition may be N,N'-diethyl-m-toluamide. The fabric substrate may be selected from the group consisting essentially of woven, non-woven and knit substrates. In one embodiment, the fabric composition further comprises the finishing agent which may be selected from the group consisting of at least (i) one reactive silicone, and/or (ii) a finishing resin, cationic softener and/or wax emulsion.

In another embodiment, the present invention relates to a fabric composition comprising a fabric substrate and an application of an insect-repellent composition, wherein the application of the insect-repellent composition comprises an aqueous dispersion consisting essentially of an amine insect-repellent, at least one reactive silicone, and starch. The aqueous dispersion is spray dried to form a powder and then the powder is applied to the fabric substrate to form the fabric composition that provides insect-repellency.

In a further embodiment, the present invention relates to a fabric composition comprising a fabric substrate and an application of an insect-repellent composition, (i) wherein the application of the insect-repellent composition comprises the steps of: (a) mixing an aqueous dispersion consisting essentially of N,N'-diethyl-m-toluamide, a substituted organosilane and silanol functional polymer, and modified corn starch; (b) spray drying the aqueous dispersion of step (a) to form a powder; (c) adding an effective amount of the powder formed in step (b) to a dye bath and dyeing said fabric substrate; (d) adding an effective amount of the powder formed in step (b) to a print paste and printing on the fabric substrate of step (c); and (e) adding an effective amount of the powder formed in step (b) to a finishing solution comprising at least two reactive silicones, and/or finishing resin and applying the finishing solution onto the fabric substrate of step (d) to form the fabric composition; (ii) wherein said fabric composition provides insect-repellency.

In still a further embodiment, the present invention relates to a method of manufacturing a fabric substrate comprising the steps of: (a) providing a fabric substrate; (b) mixing an aqueous dispersion consisting essentially of an amine insect-repellent, at least one reactive silicone, and a starch; (c) spray drying the aqueous dispersion of step (b) to form a powder; and (d) applying the powder of step (c) to the fabric substrate to form a fabric composition that provides insect repellency.

DETAILED DESCRIPTION OF THE INVENTION

Oleophilic silicone compounds, heavy alcohols (such as, for example, polyvinyl alcohol), polyvinyl acetate, liquefied synthetic rubber, or acrylic copolymers and the insect repellent N,N'-diethyl-m-toluamide (DEET) can be combined in an aqueous solution and then dried to form an insect-repellent composition. The composition has novel properties including the time-release of DEET. The rate of release of DEET may be controlled by varying the amounts of oleophilic compounds in the composition. The period of time may span from about 24 hours to about several months and may be affected by the method of storage of the powder and exposure to light and air.

Other novel properties of the composition include dispersability in water and water-based compounds (such as for example lotions, cremes, latex paints, acrylic-based paints and sealers) as well as in oil, hydrocarbon solvents and the like.

It is believed that the time-release of DEET of the present invention may be attributed to the entrapment of DEET in the resulting structure of the capsule-forming compounds and the entrapping effect of the oleophilic compounds. In one embodiment, the time-release property of DEET and the overall stability of the insect-repellent composition of the present invention may be affected by further coating the composition with, for example, a waxy compound, gelatin, polyethylene glycol and derivatives, for an intermediate coating or with, for example, clay, china or ivory, for a harder coating or a protective layer. For purposes of the present invention the term "capsule," "matrix," and "latice-like structure," will be used interchangeably and are equivalent.

In one embodiment, the insect-repellent composition of the present invention may be applied to a wide range of fabric substrates without being limited by the coarseness or smoothness of the fabric substrate. Furthermore, the insect-repellent composition of the present invention may be combined with a wide range of fabric treatment compositions. The resulting formulation may be applied to any suitable fabric substrate depending on the intended use of the fabric and the fabric treatment process such as, for example, cottons, knits, polyesters or blends, fiberglass, wovens or non-wovens and heat-sensitive substrates such as acetates and acrylates and nylon. In order to lower the insect-repellent volatility and control the loss of insect-repellent activity, the compositions may be applied such that multiple layers of super thin laminates are produced.

The insect-repellent composition of the present invention can be prepared by first formulating the insect repellent N,N'-diethyl-m-toluamide with an oleophilic chemical such as a silicone compound such as, for example, elastomeric or monomeric silicone, and then it is believed by mechanical and/or chemical entrapment of the resulting compound in a carbohydrate matrix, such as, for example, a starch compound including, but not limited to, modified corn starch, potato starch, technical starch, rice starch and any of the synthetic starches. Silicone is dissolved with DEET which is also immiscible with water. The DEET-silicone solution is mixed into a starch solution with the resulting solution being miscible in water. It is believed that the DEET molecule is entrapped in the lattice-like structure of the starch molecule that has the effect of lowering the vapor pressure of the insect repellent thus reducing its volatility. DEET is slowly released from the lattice-like structure of the starch with the net effect of the formation of an insect-repellent composition.

In one embodiment, the starch of the insect-repellent composition of the present invention has the following characteristics: 1) the starch is relatively pure (e.g. substantially free of sugars) and 2) the starch is at least partially esterified (i.e., greater than 20%). In a more specific embodiment, the starch is more substantially (>50%) esterified. In one example of this embodiment, the starch is CAPSUL®. CAPSUL® is a modified, waxy (i.e., "branched-chained") corn starch sold by National Starch and Chemical Company. Specifically, the waxy corn starch is esterified with n-octenyl succinic anhydride to form a n-octenyl succinic starch derivative.

Other starches that may be utilized in the composition of the present invention include, but are not limited to, starches such as MIRA-CAP (sold by Staley), N-LOK, and NATIONAL 46 (sold by National Starch and Chemical) and the lipophilic STA-MIST 365 and STA-MIST 7415 (sold by Staley).

In one embodiment, the silicone compound used in the present invention contains two reactive silicones. For example, the silicone compound encompasses a substituted organosilane and a silanol functional polymer. One example of a silanol functional polymer is silandiol. An example of a material that contains one reactive silicone is a product with a tradename "Hydrolast 284M."

Hydrolast 284M® is a reactive silicone system comprising two reactive silicones. Specifically for Hydrolast 294M® the reactive silicones are a reactive alkoxysilane-aminoethylminopropyltrinethoxysilane and polydimethylsiloxane. Hydrolast 284M® also contains other components such as a water-soluble organometallic tin catalyst, a carrier/solvent (e.g. water at approx 70% (w/w) of the system), surfactant, preservative/antioxidant and pH adjustment.

Other reactive silicone systems that may be used with the composition of the present invention include, but are not limited to, the following products sold by Dow Coming: Z-6020 and Z-6094 (Aminoethyl and aminopropyltrimethoxysilane), Z-6011

(3-Aminopropyltriethoxysilane), I-2304 (Chloromethyldimethylchlorosilane), Z-6010 (3-chloropropyltrichlorosilane), I-6376 (3-Chloropropyltriethoxysilane), Z-6076 (3-chloropropyltrimethoxysilane), Z-6040 (3-Glycidoxypropyltrimethoxysilane), Z-6030 (3-methacryloxypropyltrimethoxysilane), Z-1218 (Methyldicholorosilane), I-6136 (42% Octadecylaminodimethyltrimethoxysilylpropylammonium chloride and 58% MeOH), Q9-6346 (72% Octadecylalminodimethyltrimethoxysilylpropylammonium chloride and 28% MeOH), Q1-6106 (Silane-modified melamine), Q1-6083 (40% Sodium (trihydroxysilyl)-propyl methylphosponate in water), I-2333 (Trichlorosilane), Z-6032 (N-2 (Vinylbenzylamino)-ethyl-3-aminopropyltrimethoxysilane and monohydrogen chloride), Z-6075 (Vinyltriacetoxy silane), Q9-6300 (Vinyltrimetoxy silane), and Z-6026 (Z-6020 and EO/PO Glycol (dilute), 40% in methanol).

It is believed that the silicone compounds in the above embodiment provides at least two functions. First, during the mixing of the aqueous solution containing DEET, the silicone compound and the starch, the objective is to form a homogeneous emulsification. During this step, it is believed that the silicone compound acts like a surfactant by effectively emulsifying the starch, which is hydrophilic, and DEET, which is oleophilic. As such, in one embodiment, suitable silicones are oxoderivative silicones, for example, trioxo-silane and silanol. Since in one embodiment, the mixing of this aqueous solution occurs at ambient temperature, a DEET/starch/silicone emulsion is essentially produced.

Subsequently, in this embodiment, the DEET/starch/oxoderivative silicones are dried at elevated temperature such as during spray drying. During this step, it is believed that the reactive silicones, such as trioxo-organosilane and silandiol react at this elevated temperature. More specifically, in one embodiment, it is believed that, at elevated temperatures during drying, the reactive silicones undergo a condensation reaction to produce a cross-linked polymer. It is believed that the reaction progresses as follows:

a) $(RO)_3-Si-R' \rightarrow (HO)_3-Si-R'$
b) condensation of silane and silanol:

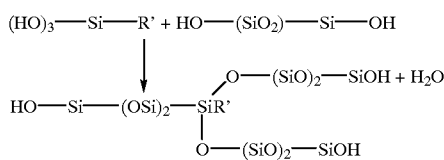

where R is any functional group.

In addition, it is believed that the end product may further undergo self-condensation. It is also believed that a cross condensation reaction with the starch may also occur.

In yet another preferred embodiment, the insect-repellent composition consists of from about 40% to about 75% weight starch, and of from about 10% to about 50% weight DEET, and of from about 15% to about 25% weight silicone. In another embodiment, the insect-repellent composition consists of from about 50% to about 72% weight starch, and of from about 20% to about 32% weight DEET and of from about 4% to 10% weight silicone, and from about 4% to about 8% weight water. In a further embodiment, the insect-repellent consists from about 30% to about 50% weight DEET. Following spray-drying, the insect-repellent composition may have a particle size from about 0.005 mm to about 1.800 mm.

In one embodiment, the insect-repellent composition of the present invention is prepared by first dissolving starch in water at its boiling point. The starch solution is then cooled to room temperature by further addition of water and the amine insect-repellent DEET and silicone are slurried into the starch solution. Following slurrying, the composition is spray dried using conventional spray drying equipment such that the slurry produces a fine white powder comprising DEET. It is to be understood that the term powder used herein includes particles ranging from about 0.0005 mm to about 1.8 mm. For purposes of the present invention, "emulsified," "slurried," "homogeneous mixture," and "dispersed" are equivalent.

As the following embodiments describe, the insect-repellent composition of the present invention may be formulated for application on fabric substrate in high yields without affecting the functionality, esthetic appearance, hand or feel of the treated substrate and leaving minimal residual odor.

In one embodiment, the insect-repellent composition may be combined with a cationic softener and applied as a finishing rinse to a fabric substrate that has been already dyed. A finishing rinse is the last rinse step in a dyeing procedure during the processing of textile material. For example, the insect-repellent composition may be combined into a formulation comprising of from about 2% to about 10% on the weight of the fabric (owf) of the insect-repellent composition of the present invention and of from about 2% to about 6% (owf) cationic softener. The term "owf" refers to on (o) weight (w) of fabric (f). This formulation may be exhausted onto the fabric substrate under mildly acidic conditions, for example using acetic acid such that the pH is of from about 5.50 to about 6.60 with the insect-repellent composition adhering to the cationic sites in dyeing and the cationic softener adhering to the fabric substrate. It should be understood that the term "finishing agent" includes chemicals or compositions added during the dyeing, printing and/or finishing step of a fabric.

In another embodiment, the insect-repellent composition may be combined in a composition comprising of from about 90% to about 150% (owf) of a padding composition and of from about 2% to about 10% (owf) of the insect-repellent composition. A padding composition refers to the mixture of 2% (owf) of the cationic softener and the insect-repellent composition that is applied to the fabric in an immersion tank and squeezed into the fabric with two or more squeeze rollers. Padding is a process of applying any chemical composition to any fabric using an immersion tank and a squeeze roller.

In yet another embodiment, the insect-repellent composition may be combined in a composition comprising of from about 90% to about 150% (owf) of a pigment printing paste composition and of from about 2% to about 10% (owf) of the insect-repellent composition. A pigment printing paste is referring to a colloidal suspension of water, melamine or acryloid binding or holding resin, synthetic thickener, pigment color or colors, and catalysts, alcohols or ammonias used during the screen printing of textiles and other substrates. It is believed that the insect-repellent composition cross-links with the pigment binder during pigment dyeing and printing to link on to the cellulose groups of the fabric substrate.

In yet a further embodiment, the insect-repellent composition of the present invention may be combined in a composition comprising of from about 90% to about 150% (owf) of water and of from about 2% to about 10% (owf) of the insect-repellent composition.

In another embodiment, the insect-repellent composition of the present invention may be used in a final rinse composition. Fabric substrates after dyeing, pigment padding and printing, with the appropriate composition which comprises the insect-repellent composition of the present invention, may be given a resin finish for hand, appearance and dimensional stability. In this particular embodiment, it is believed that the resin finish may act as a super thin laminate and provide the treated fabric with an insect-repellent finish. More particularly, when the resin used is urea-formaldehyde, it is believed that cross-linking of the molecular structure of the cotton fiber to the cellulose fiber occurs during resin curing conditions. It is further believed that the insect-repellent composition is trapped during the reaction of the urea-formaldehyde with the cellulose molecule in the cotton fabric. In one embodiment, substrate fabrics of 100% cotton and a 50%/50% polyester/cotton blend may be treated with a resin finish comprising of from about 2% to about 5% (owf) of the insect-repellent composition of the present invention and of from about 95% to about 150% (owf) of a resin finish composition.

In another embodiment, the insect-repellent composition of the present invention may be used in heat-transfer printing using a wide range of substrate fabrics. For example, of from about 2% to about 10% (owf) of the insect-repellent composition may be combined with of from about 2% to about 5% (owf) of the ink dispersion and with of from about 85% to about 96% (owf) of the extender. An ink dispersion is usually used in ink jet printing, hand screen, and semi-automatic screen printing to produce textiles with designs affixed to the textiles. An extender is usually a water-soluble alcohol or vinyl emulsion that is added to the ink to control the color level of the ink being applied and to link the ink onto the product or textile being printed. The extender can also be an organic alcohol or resin that is solvent-based. The fabric was processed by heat-transfer printing, i.e., by vaporization of the ink from the paper to the fabric at the sublimation temperature of the ink. In another embodiment, the ink dispersion can be omitted and 100% (owf) of the extender can be used. In both cases, the adhesion of the heat transfer paper to the fabric prevents the insect repellent from volatilizing and escaping resulting in greater durability.

In one embodiment, of from about 2% to about 10% (owf) of the insect-repellent composition of Example I may be combined with an extender. The fabric was processed by heat-transfer printing, i.e., by vaporization of the ink from the paper to the fabric at the sublimation temperature of the ink.

EXAMPLE I

In this example, an insect-repellent composition may be prepared by mixing into a starch slurry a mixture of silicone of about 4% weight/weight (w/w) and the insect-repellent DEET of about 8% (w/w). The starch slurry is formed by dissolving about 8% (w/w) starch into about 8% (w/w) water at its boiling point. The mixture of insect repellent and silicone is added to the starch mixture after cooling the slurry to room temperature.

The resultant slurry is spray dried in a spray drying chamber at an inlet temperature of about 230° F. using an atomizing force of from about 2400 to about 3200 psig from an atomizer. The slurry produces a fine white powder comprising of from about 0.1% to about 32% (w/w) DEET and with of from about 4% to about 8% (w/w) moisture.

EXAMPLE II

From about 2% to about 10% (owf) of the insect-repellent composition of Example I can be combined with of from about 3% to about 6% (owf) cationic softener and exhausted on a fabric substrate that has been dyed on a jig, beck, beam or jet at about 120° F., for about fifteen (15) minutes and at a pH of from about 5.50 to about 6.60, adjusted with acetic acid.

EXAMPLE III

From about 2% to about 10% (owf) of the insect-repellent composition of Example I can be combined with a pigment padding composition of about 0.06% (owf) of a aqueous ammonia, about 4.78% (owf) of a padding emulsion (for example, padding emulsion #8908 from BASF), about 2.39% (owf) of a antimigrant (for example, antimigrant #09–99515 from BASF), about 0.48% (owf) ammonium sulphate, water, and a variable weight percent of a pigment dye depending on the shade. The resulting composition is padded onto the fabric at from about 85% to about 150% (owf) wet-pickup, dried at about 275° F. and cured at about 340° F. for about thirty (30) seconds.

EXAMPLE IV

From about 2% to about 10% (owf) of the insect-repellent composition of Example I can be combined with a pigment printing composition of about 4.7% (owf) of a dispersion of an acrylic copolymer in mineral oil (for example, Allied DP3-5205 from Allied Colloids, Inc.), about 10% (owf) of a white aqueous-based acrylate copolymer emulsion (for example, Allied PB-8A from Allied Colloids, Inc.), about 83.3% (owf) water, and a variable weight percent of a pigment print dye depending on the shade. The resulting composition is printed onto the fabric in all colors of the pattern and cured at about 340° F. for about sixty (60) seconds.

EXAMPLE V

From about 2% to about 10% (owf) of the insect-repellent composition of Example I can be combined with a water repellent composition of from about 3% to about 6% (owf) silicone softener, about 6% (owf) wax emulsion (for example, fluoropolymer wax emulsion PEL-TEK 508, Hydrolabs, Inc.), and of from about 4% to about 7% (owf) of a glyoxal reactant (for example, REACTEX #7222 from Ivax Industries, Inc.). The resulting composition is padded onto the fabric at from about 85% to about 150% (owf) wet-pickup, dried at about 275° F. and cured at about 340° F. for about twenty (20) seconds.

EXAMPLE VI

From about 2% to about 10% (owf) of the insect-repellent composition of Example I can be combined with a resin finishing composition suitable for treating 100% cotton and comprising of from about 3% to about 6% (owf) of the cationic softener, of from about 1% to about 2% (owf) of the silicone softener, and of from about 4% to about 7% (owf) of the glyoxal reactant.

From about 2% to about 10% (owf) of the insect-repellent composition of Example I can also be combined with a resin finishing composition suitable for treating 50%/50% polyester/cotton and comprising of from about 3% to about 6% (owf) of the cationic softener, of from about 1% to about 2% (owf) of the silicone softener, and of from about 2% to about 4% (owf) of the glyoxal reactant.

The resin finishing composition may be applied to a fabric substrate that has been dyed, pigment padded, and/or printed as in the above Examples. The resin finish acts as a super thin laminate and provides an additional insect-repellent coating.

With both formulas and fabrics, the resulting composition is padded onto the fabric at from about 85% to about 150% (owf) wet pickup, dried at about 275° F. and cured at about 340° F. for about twenty (20) seconds.

EXAMPLE VII

From about 2% to about 10% (owf) of the insect-repellent composition of Example I can be combined with about 20% (owf) of the ink dispersion and about 75% (owf) of the extender. The fabric was processed by heat-transfer printing, i.e., by vaporization of the dye from the paper to the fabric at the sublimation temperature of the dye.

EXAMPLE VIII

From about 2% to about 10% (owf) of the insect-repellent composition of Example I can be combined with about 100% extender. The fabric was processed by heat-transfer printing, i.e., by vaporization of the dye from the paper to the fabric at the sublimation temperature of the dye.

EXAMPLE IX

An insect-repellent composition was prepared by first dissolving about 8% (w/w) of modified corn starch ("CAPSUL" from National Starch and Chemical) into about 80% (w/w) water at its boiling point. After cooling the starch slurry to room temperature, about 8% (w/w) of DEET and about 4% (w/w) of reactive silicone containing substituted silane and silandiol ("Hydrolast 284M") were added. The mixture was agitated until a homogeneous mixture was obtained.

The resultant slurry was spray dried in a spray drying chamber at about 230° F. The slurry produced the insect-repellent composition in the form of a white powder comprising between about 20% to about 32% (w/w) of DEET.

The insect-repellent composition was added to a dye bath to produce a dye bath containing about 3% (owf) of DEET. A white fabric substrate of 100% cotton was immersed in the dye bath and allowed to come to equilibrium with the dye bath. The fabric substrate was removed from the dye bath.

Subsequently, the dyed fabric containing about 3% (owf) of DEET was combined with a pigment printing formulation having the insect-repellent composition containing about 3% (owf) of DEET. The resulting formulation was printed onto the fabric in all colors to produce a camouflage pattern.

The fabric composition was then combined with a resin finishing composition containing about 3% (owf) of Hydrolast 284M, about 5% (owf) of urea-formaldehyde resin, and the insect-repellent composition containing about 5% (owf) of DEET. The fabric composition was squeeze-rolled and dried at about 300° F.

It should be understood that Example IX above can be modified to involve applying the insect-repellent composition of the present invention at one or more of the individual steps—dyeing, printing, and/or finishing.

Field Testing

The insect-repellent compositions of the present invention were found to afford the wearer complete protection under most types of weather and infestation conditions. Furthermore, the insect-repellency effectiveness of the fabric substrate treatment was found to span up to a period of about several hours to at least several weeks.

To test the stability of the fabric treatment, garments were produced from treated fabric. Fabric substrates which were laundered from ten (10) to fifty (50) launderings continue to exhibit insect-repellent properties. It is to be noted that typically the industry standard number of washings for apparel is three (3), five (5), or ten (10) for consumer apparel and fifty (50) washings for military or certain specialty requirements such as, for example, flame retardancy.

To test the effectiveness of the treatment, laboratory size knit and woven fabric samples were processed using the compositions described above. A first batch of the samples were tested for direct insect repellency using fire ants and fruit flies as test insects. For several hours the fire ants and fruit flies were directly repelled by the fabric samples. A second batch of the fabric samples were tested by wearers who wore shirts made from the fabric sample. Mosquitoes and blackflies were repelled for at least eleven (11) hours during a fishing trip.

A production trial was initiated on four (4) fabric substrates, knit and woven cotton, poly/cotton and poly/nylon. The fabrics were dyed with the insect-repellent composition applied during dyeing and/or resin finishing. Another group of knitted and woven fabrics were pad dyed, printed and resin finished with the insect-repellent composition applied at the dyeing, printing and resin finishing steps.

Garments such as shirts, hats, and the like were produced from the treated fabric substrates. The garments were tested under conditions encountered during outdoor activities. The garments were found to repel insects under outdoor conditions during activities such as hiking, hunting, and fishing in coastal, piedmont and mountain conditions during day and night wear. The treated garments were compared to untreated counterparts under the same conditions. In one particular field trial, garments were tested on mosquitoes. The mosquitoes would land on exposed skin and promptly bite. By contrast, when the mosquitoes landed on the treated fabric at any location on the garment, they would only remain for about four (4) to about six (6) seconds before taking off.

This present invention and many of its attendant advantages will be understood from the foregoing description, and it will be apparent that various modifications and changes can be made without departing from the spirit and scope of the present invention or sacrificing all of its material advantages, the process hereinbefore described being merely preferred embodiments.

For example, the insect-repellent composition of the present invention can incorporate different insect control agents such as, for example, alkylamines and alkylneodecamines. Additionally, the insect-repellent composition may be applied on a wide range of fabric substrates including but not limited to textile blends, woven and non-woven, knits, fibers, leather and synthetic adaptations of leather, flocked-fabrics, wood and wood derivatives, plastic and laminates, cable, sheeting, film fiberglass and plexiglass. The insect-repellent composition may also be comprised in moth proofing composition, packaging material, and paint compositions. Furthermore, a longer-term repellency can be obtained when such capsules are used in the manufacture of commercial finishes such as caulking compositions, paint sealers, wall and floor coverings and the like. Additionally, the compositions of the present invention can have a wide applicability in situations requiring a lower concentration of DEET. As an example, the insect-repellent composition may be incorporated with a scent or a fragrance or pheromones or with any other compositions that could be conducive to applications in sporting, farming, or hunting situations. Conversely, higher concentrations of up to from about 20% to about 25% of the insect-repellent composition can be used in caulking compounds.

The present invention may be embodied in other specific forms without departing from its spirit or essential attributes. Accordingly, reference should be made to the appended claims, rather than the foregoing specification, as indicating the scope of the present invention.

What is claimed is:

1. An article of manufacture comprising (i) a fabric substrate and (ii) an insect-repellant composition, wherein said insect-repellant composition is prepared as an aqueous consisting essentially of an amine insect-repellant, at least two reactive silicones soluble with said amine insect-repellant, and starch; said insect-repellant composition being dried into a powder and applied to said fabric at from about 2% to about 30% on weight of fabric (owf), to form said article of manufacture having insect repellancy.

2. The article of manufacture of claim 1 wherein at least one finishing agent is added to said powder before application onto said fabric substrate.

3. The article of manufacture of claim 1 wherein said application of said insect-repellant composition comprises the step of adding an effective amount of said powder to a dye bath and dyeing said fabric substrate.

4. The article of manufacture of claim 3 wherein said application of said insect-repellant composition further comprises the step of adding an effective amount of said powder to a print paste and printing on said fabric substrate.

5. The article of manufacture of claim 4 wherein said application further comprises the step of adding an effective amount of said powder to a finishing solution, said finishing solution comprising at least one reactive silicone and applying said finishing solution to said fabric substrate to form said fabric composition.

6. The article of manufacture of claim 1 wherein said starch of said insect-repellant composition is a modified starch.

7. The article of manufacture of claim 1 wherein said amine insect-repellant of said insect-repellant composition is N,N'-diethyl-m-toluamide.

8. The article of manufacture of claim 7 wherein N,N'-diethyl-m-toluamide consists from about 1% to about 15% (owf).

9. The article of manufacture of claim 1 wherein said fabric substrate is selected from the group consisting of woven, non-woven and knit substrates.

10. The article of manufacture of claim 2 wherein said finishing agent comprises at least a finishing agent, a softener and a wax emulsion.

11. The article of manufacture of claim 1 wherein said finishing agent is selected from the group consisting of glyoxal resins, urea-formaldehyde resins, acrylic resins, polyvinyl acetates, polyvinyl alcohols, melamine, and fluorocarbon resins.

12. The article of manufacture of claim 1 wherein said fabric composition has insect-repellant efficacy for at least one week.

13. An article of manufacture comprising (i) a fabric substrate and (ii) an insect-repellant composition applied to said substrate, wherein said article of manufacture is prepared by the steps of:

(a) mixing an aqueous dispersion consisting essentially of N,N'-diethyl-m-tolumide, a reactive silane, and starch; and (b) spray drying said aqueous dispersion of step (a) to form a powder;

wherein said article of manufacture has insect-repellancy, and said insect-repellent composition being present on said substrate from about 2% to about 30% (owf).

14. The fabric composition of claim 13 wherein said fabric composition has insect-repellant efficacy for at least one week.

15. An article of manufacture as in claim 13 further comprising the steps of adding an effective amount of said powder formed in step (b) to a dye bath and dyeing said fabric substrate.

16. An article of manufacture as in claim 13 further comprising the steps of adding an effective amount of said powder formed in step (b) to a print paste and printing with said print paste on said fabric substrate.

17. An article of manufacture as in claim 13 further comprising the steps of adding an effective amount of said powder formed in step (b) to a finishing solution comprising a finishing agent and applying the finishing solution to said fabric substrate.

* * * * *

UNITED STATES PATENT AND TRADEMARK OFFICE
CERTIFICATE OF CORRECTION

PATENT NO. : 6,015,570
DATED : January 18, 2000
INVENTOR(S) : Tucci et al.

It is certified that error appears in the above-identified patent and that said Letters Patent is hereby corrected as shown below:

Title page,
Item [54], delete "COMPOSITONS AND USES" and insert therefor -- FABRIC COMPOSITION AND RELATED METHODS --

Related U.S. Application Data, delete "Dec. 12, 1994" and insert therefor -- Dec. 12, 1996 --.

Column 1,
Line 2, delete "COMPOSITONS AND USES" and insert therefor -- FABRIC COMPOSITION AND RELATED METHODS --
Line 7, delete "Dec. 22, 1994" and insert therefor -- Dec. 12, 1996 --.

Column 2,
Line 43, delete "aqueous" and insert therefor -- insect-repellent --.
Line 43, delete "formed by an insect-repellent" and insert therefor -- formed by an aqueous --.

Column 3,
Lines 59-60, delete "latice-like" and insert therefor -- lattice-like --.

Column 4,
Line 53, delete "one reactive silicone" and insert therefor -- two reactive silicones --.
Line 57, delete "294M®" and insert therefor -- 284M® --.
Line 58, delete "aminoethylminopropyltrinethoxysilane" and insert therefor
-- aminoethylaminopropyltrimethoxysilane --.
Line 65, delete "Coming" and insert therefor -- Corning --.

Column 5,
Line 9, delete "Octadecylalminodi-" and insert therefor -- Octadecylaminodi- --.
Line 47, delete "$(Osi)_2$" and insert therefor -- $(Osi)_2O$ --.

Column 11,
Lines 8, 9, 10, 12, 20, 24, and 34, delete "insect-repellant" and insert therefor -- insect-repellent --.
Line 9, after "aqueous" insert -- dispersion --.
Line 12, delete "repellant" (first occurrence) and insert therefor -- repellent --.
Line 15, delete "repellancy" and insert therefor -- repellency --.
Line 37, delete "insect-repellant" (first occurrence) and insert therefor -- insect-repellent --.
Line 37, delete "insect-repellant" (second occurrence) and insert therefor -- insect-repellent --.

UNITED STATES PATENT AND TRADEMARK OFFICE
CERTIFICATE OF CORRECTION

PATENT NO.    : 6,015,570
DATED         : January 18, 2000
INVENTOR(S)   : Tucci et al.

It is certified that error appears in the above-identified patent and that said Letters Patent is hereby corrected as shown below:

Column 12,
Line 11, 14, and 27, delete "insect-repellant" and insert therefor -- insect-repellent --.
Line 19, delete "N,N'-diethyl-m-tolumide" and insert therefor -- N,N'-diethyl-m-toluamide --.
Line 23, delete "insect-repellancy" and insert therefor -- insect-repellency --
Line 26, delete "fabric composition" and insert therefor -- article of manufacture --.

Signed and Sealed this

Twenty-seventh Day of November, 2001

Attest:

NICHOLAS P. GODICI
Attesting Officer        Acting Director of the United States Patent and Trademark Office